US00PP30359P2

(12) United States Plant Patent
Kardos et al.

(10) Patent No.: US PP30,359 P2
(45) Date of Patent: Apr. 9, 2019

(54) ***HYDRANGEA* PLANT NAMED 'BAILMACFIVE'**

(50) Latin Name: *Hydrangea macrophylla*
Varietal Denomination: Bailmacfive

(71) Applicant: Bailey Nurseries Inc, Newport, MN (US)

(72) Inventors: Joshua Kardos, Asheville, NC (US); Michael A. Dirr, Bogart, GA (US); Rhonda Helvick, Madison, GA (US); Oren McBee, Bishop, GA (US)

(73) Assignee: BAILEY NURSERIES INC., Newport, MN (US)

( * ) Notice: Subject to any disclaimer, the term of this patent is extended or adjusted under 35 U.S.C. 154(b) by 11 days.

(21) Appl. No.: 15/731,992

(22) Filed: Sep. 5, 2017

(51) Int. Cl.
*A01H 5/02* (2018.01)

(52) U.S. Cl.
USPC ..... Plt./250
CPC ..... *A01H 5/02* (2013.01)

(58) Field of Classification Search
USPC ..... Plt./250
See application file for complete search history.

*Primary Examiner* — Anne Marie Grunberg
(74) *Attorney, Agent, or Firm* — Penny J. Aguirre

(57) ABSTRACT

A new cultivar of *Hydrangea macrophylla* named 'Bailmacfive' that is characterized by its mophead inflorescences that bloom on old and new wood and exhibits remontant blooming, its inflorescences that are pink-red in color or purple in color depending on the pH levels of the soil and its compact plant habit.

2 Drawing Sheets

Botanical classification: *Hydrangea macrophylla.*
Varietal denomination: 'Bailmacfive'.

BACKGROUND OF THE INVENTION

The present invention relates to a new and distinct cultivar of *Hydrangea macrophylla* and will be referred to hereafter by its cultivar name, 'Bailmacfive'. 'Bailmacfive' represents a new mophead type *Hydrangea*, a deciduous shrub grown for use as a landscape plant.

'Bailmacfive' was derived from an ongoing breeding program conducted by the Inventors in Watkinsville, Ga. The objectives of the breeding program are to develop new cultivars of *Hydrangea macrophylla* with compact plant habits, inflorescences that are red in color, re-blooming, and bloom on old and new wood, and that are cold hardy in U.S.D.A. Zone 4.

'Bailmacfive' originated from a cross-made in May of 2013 between *Hydrangea macrophylla* cultivars 'Hot Red' (not patented) as the female parent and 'PIIHM-II' (U.S. Plant Pat. No. 25,566) as the male parent. 'Bailmacfive' was selected as a single unique plant in June of 2014 from amongst the resulting seedlings.

Asexual propagation of the new cultivar was first accomplished by softwood stem cuttings by one of the Inventors in Watkinsville, Ga. in July of 2014. Asexual propagation by softwood stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bailmacfive' as a unique cultivar of *Hydrangea.*

1. 'Bailmacfive' exhibits mophead inflorescences that bloom on old and new wood and exhibits remontant blooming.
2. 'Bailmacfive' exhibits inflorescences that are pink-red in color or purple in color depending on the pH levels of the soil and available aluminum.
3. 'Bailmacfive' exhibits a compact plant habit.

The female parent of 'Bailmacfive', 'Hot Red', differs from 'Bailmacfive' in having a less compact plant habit with a shorter mature plant size, inflorescences that are red to violet in color and in being less cold hardy. The male parent of 'Bailmacfive', 'PIIHM-II', differs from 'Bailmacfive' in having longer internodes, a less compact plant habit, inflorescences that are dark pink in color or violet-purple depending on the pH levels of the soil, stems that are red in color and leaves that are darker green in color. 'Bailmacfive' can be most closely compared to the *Hydrangea macrophylla* cultivars 'Alpenhluhen' (not patented) and 'Pia' (not patented). 'Alpenhluhen' is similar to 'Bailmacfive' in having flowers that are pink-red in color. 'Alpenhluhen' differs from 'Bailmacfive' in having inflorescences that do not re-bloom, in requiring more nodes of growth to bloom, in having shorter internodes and in being less cold hardy. 'Pia' is similar to 'Bailmacfive' in having inflorescences that are red-pink in color. 'Pia' differs from 'Bailmacfive' in requiring more nodes of growth to bloom, and in being less cold hardy.

BRIEF DESCRIPTION OF THE DRAWINGS

The accompanying colored photographs illustrate the overall appearance and distinct characteristics of the new *Hydrangea*. The photographs were taken of a two year-old plant of 'Bailmacfive' as grown outdoors in a in a greenhouse in Cottage Grove, Minn.

The photograph in FIG. 1 provides a top view of a plant of 'Bailmacfive' in bloom.

Figure 1:
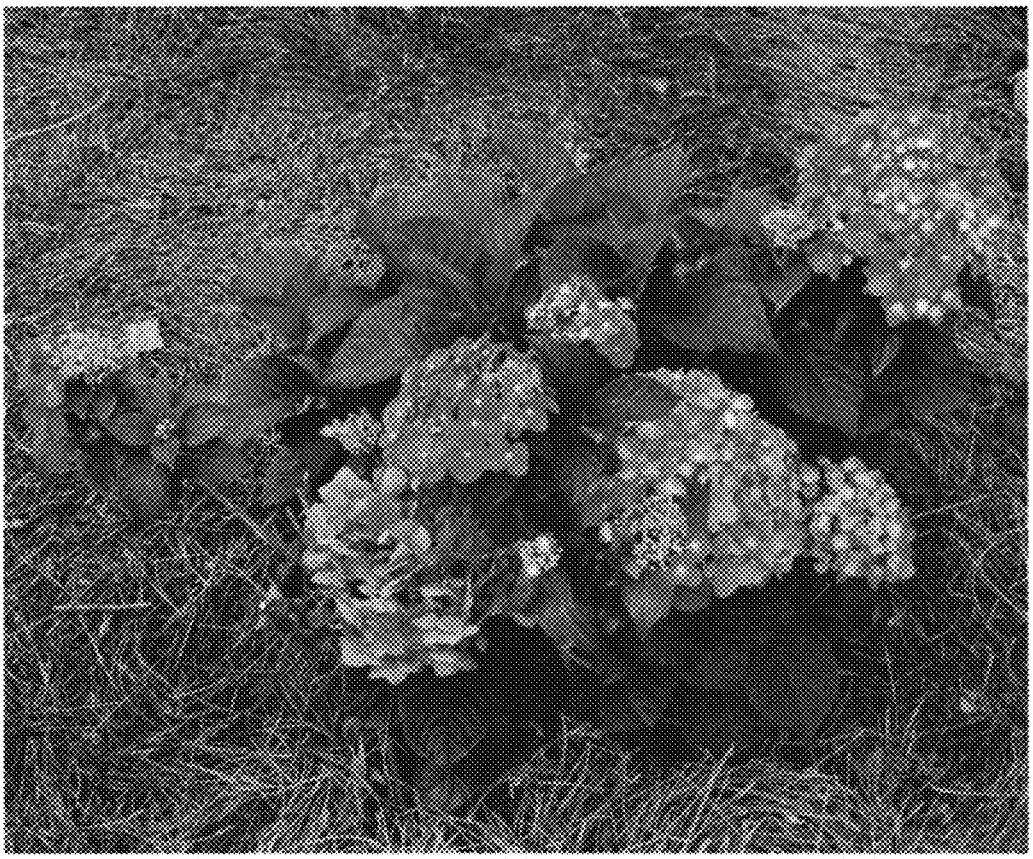
Figure 2:
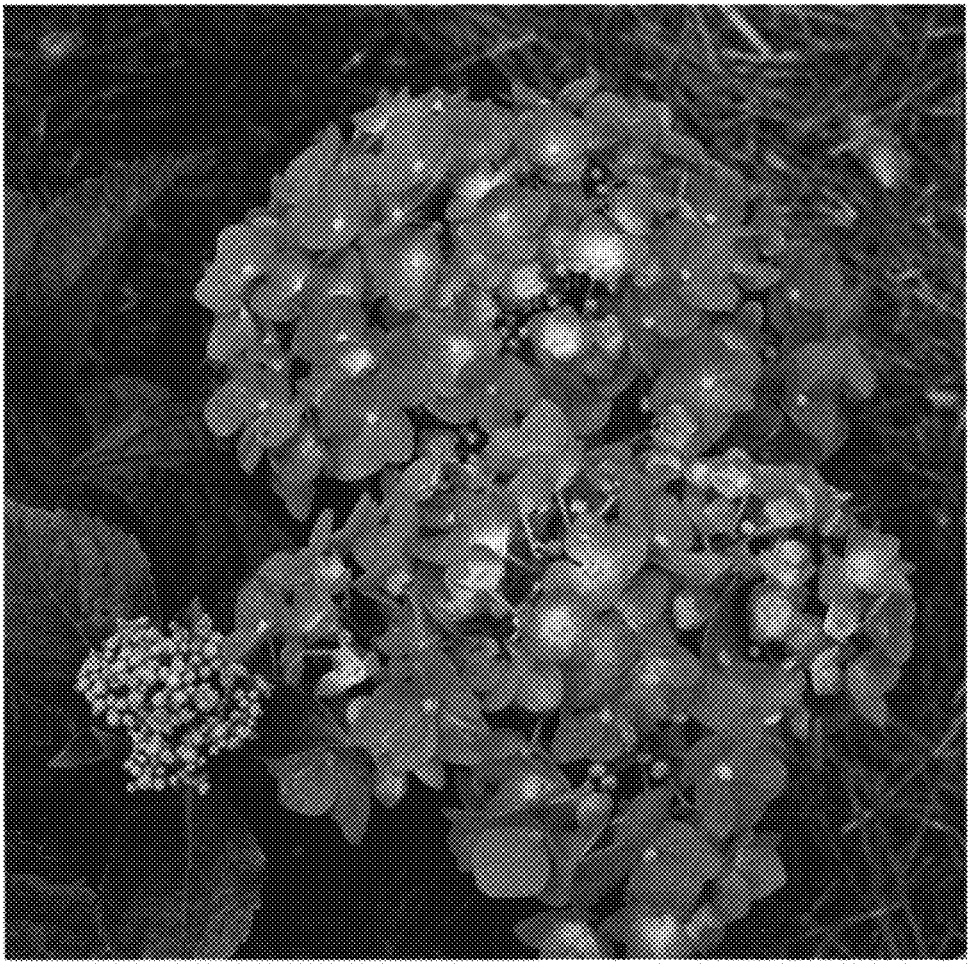

The photograph in FIG. 2 provides a close-up view of the inflorescences of 'Bailmacfive'.

The colors in the photographs may differ slightly from the color values cited in the detailed botanical description, which accurately describe the colors of the new *Hydrangea.*

BOTANICAL DESCRIPTION OF THE PLANT

The following is a detailed description of two year-old plants of 'Bailmacfive' as grown outdoors in 2-gallon containers in a greenhouse in Cottage Grove, Minn. Plants were grown in alkaline soils. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Commences in June and blooms until freeze in Minnesota, blooms on new wood and old wood and re-blooming.

*Plant type.*—Deciduous shrub, mophead type *Hydrangea.*

*Plant habit.*—Broadly upright to outward.

*Height and spread.*—Reaches about 35 cm in height and 60 cm in spread as grown in a 2-gallon container, reaches an average of 60 cm in height and spread as a 2 year-old plant in the landscape.

*Cold hardiness.*—At least to U.S.D.A. Zone 4.

*Diseases.*—No resistance or susceptibility to diseases has been observed.

*Root description.*—Fine and fibrous, 199B in color.

*Propagation.*—Softwood stem cuttings.

*Growth rate.*—Moderate.

*Root development.*—Softwood cuttings root readily in 6 weeks, rooted cuttings are overwintered and roots will fully develop in a one-quart container by midsummer the following year.

Stem description:

*Stem shape.*—Rounded.

*Stem strength.*—Strong.

*Stem color.*—Young and mature; 143C with 187A at the top nodes, old growth at the base; a blend of N200A to 199A.

*Stem size.*—Average of 32 cm in length and 8 mm in diameter.

*Stem surface.*—Younger and mature stems; glabrous, sparsely to moderately lenticellate, lenticles; 5 per $cm^2$, an average of 1.5 mm in length and 1 mm in width, 200A in color, old growth at base; bark-like, rugose, slightly peeling.

*Internode length.*—Average of 4 cm.

*Branching.*—Average of 10 lateral branches.

*Stipules.*—Persistent, 2 opposite at base of petioles, stipule bud; is 5 mm in length, 3 mm in width, 143A in color, flushed with 184A in color, oblong in shape, acute apex, glossy and glabrous surface, stipule leaves; 8 leaves inside stipule, 2.5 cm in length, 1 cm in width, acute apex, serrate margins, each leaf fused into base, opposite, both surfaces glossy, both surface 143A in color, veins match surface color.

Foliage description:

*Leaf shape.*—Ovate to broad ovate.

*Leaf arrangement.*—Opposite.

*Leaf division.*—Simple.

*Leaf base.*—Short attenuate.

*Leaf apex.*—Broad apiculate.

*Leaf margins.*—Serrate.

*Leaf venation.*—Pinnate, upper surface; 144B, lower surface; 145B in color.

*Leaf size.*—Matures to an average of 12 cm in length and 9 cm in width.

*Leaf attachment.*—Petiolate.

*Leaf surface.*—Upper surface; very slightly glossy to dull, lower surface; dull.

*Leaf color.*—Young and mature upper surface; between NN137A and 137A, young and mature lower surface; between 138A and 138B.

*Petioles.*—An average of 2 cm in length and 4 mm in diameter, upper and lower surface 144B in color, both surfaces glabrous and dull.

Inflorescence description:

*Inflorescence type.*—Terminal panicle, mophead in form comprised of inconspicuous fertile flowers surrounded by numerous single sterile flowers.

*Lastingness of inflorescence.*—Persistent for 6 months.

*Inflorescence number.*—One per lateral.

*Inflorescence size.*—Young; 8 cm in height, 12 cm in diameter, mature; Average of 13 cm in height and 19 cm in diameter.

*Flower number.*—Average of 160 sterile flowers and 45 fertile flowers per panicle.

*Flower fragrance.*—None.

*Flower aspect.*—Upright to outward.

*Flower size.*—Sterile flowers; an average of 5 cm in diameter and 1 mm in depth, fertile flowers; an average of 1 cm in diameter and depth.

*Flower type.*—Rotate.

*Flower buds.*—Sterile flowers; average of 3 mm in length and 4 in diameter, obovate in shape, color is 142C with hints of N57A, fertile flowers; average of 3 mm in width and 2 mm in diameter, broad obovate in shape, color is a blend of 67A and 69A.

*Peduncles.*—Young; strong, average of 1 cm in length and 2 mm in width, surface is dull and moderately covered with very fine woolly hairs that match surface color to NN155A in color and too small to measure, color; 145C, flushed and spotted with 59A and 60A, mature; strong, average of 1.5 cm in length and 2 mm in width, surface is dull and moderately covered with very fine woolly hairs that match surface color to NN155A in color and too small to measure, color; 146C, flushed and spotted with N187A and 187A.

*Pedicels.*—Sterile flowers; young; moderately strong, average of 2 cm in length and 1 mm in width, surface is dull and moderately covered with very fine woolly hairs that match surface color and too small to measure, color; a blend of 63A, 63B and 145D, mature; strong, average of 3 cm in length and 2 mm in width, surface is dull and moderately covered with very fine woolly hairs that match surface color to NN155A in color and too small to measure, color; 186A to 186B, fertile flowers; young; an average of 5 mm in length and 1 mm in diameter, moderate strength, 63A in color, surface is dull and glabrous, mature; strong, average of 3 mm in length and 1 mm in width, surface is dull and moderately covered with very fine woolly hairs that match surface color to NN155A in color and too small to measure, color; 186A.

*Petals.*—Sterile flowers; before opening; petal spot; 3 mm in diameter, round in shape, glabrous surface, young color is 140B, mature color is a blend of 62B and 49C, when fully open; 3 mm in length and width, both surfaces are satiny and dull, acute apex, rotate arrangement, cuneate base, entire margins, ovate and concave in shape, inner and outer surface color center is a blend of 68A and 76B to 76C, margins, tips and base are 76B to 76C, fertile flowers; an average of 4, rotate arrangement, acute apex, cuneate base, entire margins, ovate and concave in shape, an average of 4 mm in length, 2 mm in width, upper and lower surface; glabrous, color; upper surface when opening and fully opened 67A, with margins and base 69A, lower surface when opening and fully opened; a blend of 67A and 69A.

*Flower tube/calyx.*—Fertile flowers; 4 mm in length, 2 mm in width, 69A in color.

*Sepals.*—Sterile flowers; average of 4 to 6, broad rhomboidal to deltoid in shape, moderately to strongly overlapping, rotate in arrangement, entire margin, apex is very slightly retuse, cuneate base, average of 2 cm in length and width, upper and lower surface glabrous and satiny, color: upper surface when opening; 145A fused with N57A at the tips, upper surface when young and fully open; center is N57C, mid-section is N57A, tips are slightly 63A, veins match surface colors, upper surface when mature and fully open; 185A, veins match surface color, upper surface when dry; a blend of 90A and 91C and N82A, base and tip flushed with 10A, veins match surface color, lower surface when opening; 145C fused with N57A at the tips, veins match surface color, lower surface when young and fully open; a blend of 60D and 61D and 69C, veins 63A, lower surface when mature and fully open; 185C with a light undertones of 159B, veins are 63B, lower surface when dry; base is 91C and flushed with 10A, mid-section is 90C, tip and edges are 83A, veins match surface color, fertile flowers; 5, rotate in arrangement, ovate in shape, entire margin, acute apex, cuneate base, average of 0.5 mm in length and 1 mm in width, both surfaces are glabrous, color of upper and lower surface 11C.

Reproductive organs: (Present on fertile flowers and occasionally on sterile flowers).

*Stamens.*—Sterile flowers; emerging from petal spot; average of 8, anther; broad reniform in shape, 1 mm in length and width, 157A in color, filament; 4 mm in length, 0.5 mm in width and 65B in color, pollen is low to moderate in quantity and 11C in color, fertile flowers; average of 10, anther is broad reniform in shape, 0.5 mm in length and NN155A in color with side stripes of 200A, filament is 5 mm in length and 68B in color, pollen is low to moderate in quantity and 11C in color.

*Pistils.*—Sterile flowers; emerging from petal spot; 2, average of 2 mm in length, 0.5 mm in width, stigma is clavate in shape and NN155A in color, 0.5 mm in length and diameter, style is an average of 1.5 mm in length and a blend of 63B and NN155A in color, ovary is NN155A in color and inferior, fertile flowers; average of 3, an average of 2 mm in length, stigma is clavate in shape and 69B in color, style is 67A in color, ovary is NN155A in color and inferior.

*Fruit and seed.*—Not observed.

It is claimed:

1. A new and distinct cultivar of *Hydrangea* plant named 'Bailmacfive' substantially as herein illustrated and described.

* * * * *